US011310211B2

(12) United States Patent
Schneider et al.

(10) Patent No.: US 11,310,211 B2
(45) Date of Patent: Apr. 19, 2022

(54) SECURELY SHARING DATA BETWEEN A HEARING DEVICE, HEARING DEVICE USER, AND DATA STORAGE

(71) Applicant: Sonova AG, Staefa (CH)

(72) Inventors: Philipp Schneider, Zürich (CH); Aliaksei Tsitovich, Staefa (CH); Filip Wojcieszyn, Staefa (CH); Daniel Schmid, Brugg (CH)

(73) Assignee: Sonova AG, Staefa (CH)

( * ) Notice: Subject to any disclaimer, the term of this patent is extended or adjusted under 35 U.S.C. 154(b) by 339 days.

(21) Appl. No.: 16/016,766

(22) Filed: Jun. 25, 2018

(65) Prior Publication Data

US 2019/0379644 A1 Dec. 12, 2019

(30) Foreign Application Priority Data

Jun. 6, 2018 (EP) .................................... 18176351

(51) Int. Cl.
| | |
|---|---|
| *H04L 29/06* | (2006.01) |
| *G16H 40/67* | (2018.01) |
| *H04L 9/08* | (2006.01) |
| *H04L 61/50* | (2022.01) |
| *H04L 67/06* | (2022.01) |
| *H04W 12/02* | (2009.01) |
| *H04L 101/618* | (2022.01) |

(52) U.S. Cl.
CPC ......... *H04L 63/0435* (2013.01); *G16H 40/67* (2018.01); *H04L 9/0819* (2013.01); *H04L 9/0894* (2013.01); *H04L 61/20* (2013.01);
*H04L 67/06* (2013.01); *H04W 12/02* (2013.01); *H04L 61/6018* (2013.01)

(58) Field of Classification Search
CPC ..... H04L 63/0435; H04L 67/06; H04L 61/20; H04L 9/0894; H04L 9/0819; H04L 61/6018; H04W 12/02; G16H 40/67; H04R 25/55; H04R 25/70; H04R 2225/55
See application file for complete search history.

(56) References Cited

U.S. PATENT DOCUMENTS

| | | | |
|---|---|---|---|
| 6,556,686 B1 | 4/2003 | Weidner et al. | |
| 8,166,312 B2 * | 4/2012 | Waldmann | ............. H04R 25/70 713/189 |
| 8,296,826 B1 * | 10/2012 | Bartolucci | ............. H04L 67/06 726/4 |
| 9,219,966 B2 | 12/2015 | Wang et al. | |
| 9,332,358 B2 * | 5/2016 | Waldmann | .......... H04L 43/0876 |

(Continued)

FOREIGN PATENT DOCUMENTS

WO 2016078710 5/2016

*Primary Examiner* — Saleh Najjar
*Assistant Examiner* — Nhan Huu Nguyen
(74) *Attorney, Agent, or Firm* — ALG Intellectual Property, LLC (57) ABSTRACT

The disclosed technology relates to securely sharing data between a hearing care professional (HCP) and a hearing device user. For example, the disclosed technology relates to securely accessing fitting data for a hearing device. The disclosed technology includes a hearing device that has a memory, where the memory stores a key that can be used for encryption and decryption. The key can be a symmetrical key. In addition to storing a key, the hearing device can store a uniform resource indicator (URI) in its memory.

16 Claims, 5 Drawing Sheets

(56) References Cited

U.S. PATENT DOCUMENTS

| Patent/Pub No. | Date | Inventor | Classification |
|---|---|---|---|
| 9,398,385 B2 * | 7/2016 | Schneider | H04R 25/70 |
| 9,608,807 B2 * | 3/2017 | Pedersen | H04L 63/1483 |
| 9,887,848 B2 * | 2/2018 | Pedersen | H04L 63/0876 |
| 10,027,474 B2 * | 7/2018 | Pedersen | H04L 63/123 |
| 10,045,207 B2 * | 8/2018 | Pedersen | H04L 63/1441 |
| 10,057,694 B2 * | 8/2018 | Pedersen | H04R 25/554 |
| 10,104,522 B2 * | 10/2018 | Pedersen | H04W 4/80 |
| 2003/0165239 A1 * | 9/2003 | Bantz | H04L 9/3231 |
| | | | 380/53 |
| 2010/0205447 A1 * | 8/2010 | Waldmann | H04R 25/70 |
| | | | 713/182 |
| 2011/0289316 A1 * | 11/2011 | Cremin | G06F 21/31 |
| | | | 713/168 |
| 2012/0308034 A1 * | 12/2012 | El-Hoiydi | H04B 7/0822 |
| | | | 381/77 |
| 2013/0024798 A1 * | 1/2013 | Schneider | H04R 25/70 |
| | | | 715/771 |
| 2013/0322669 A1 * | 12/2013 | Boretzki | H04R 25/70 |
| | | | 381/314 |
| 2014/0211973 A1 * | 7/2014 | Wang | H04R 25/505 |
| | | | 381/315 |
| 2014/0334629 A1 * | 11/2014 | Andersen | H04R 25/70 |
| | | | 381/60 |
| 2014/0341382 A1 * | 11/2014 | Waldmann | H04R 25/30 |
| | | | 381/60 |
| 2015/0319557 A1 * | 11/2015 | El-Hoiydi | H04L 1/08 |
| | | | 455/41.2 |
| 2016/0157026 A1 * | 6/2016 | Guindi | H04R 25/305 |
| | | | 381/60 |
| 2016/0173278 A1 * | 6/2016 | Pedersen | H04L 63/1483 |
| | | | 380/255 |
| 2016/0173462 A1 * | 6/2016 | Pedersen | H04W 12/02 |
| | | | 713/171 |
| 2016/0212552 A1 * | 7/2016 | Schneider | H04L 67/06 |
| 2016/0337769 A1 * | 11/2016 | Siddhartha | H04R 25/558 |
| 2016/0357537 A1 * | 12/2016 | Falkenburg | H04L 67/06 |
| 2017/0004290 A1 * | 1/2017 | Pedersen | H04R 25/70 |
| 2017/0005810 A1 * | 1/2017 | Pedersen | H04W 12/069 |
| 2017/0006024 A1 * | 1/2017 | Pedersen | G06F 21/34 |
| 2017/0006029 A1 * | 1/2017 | Pedersen | H04W 4/80 |
| 2017/0006391 A1 * | 1/2017 | Pedersen | H04R 25/505 |
| 2017/0054528 A1 * | 2/2017 | Pedersen | H04L 1/08 |
| 2017/0064545 A1 * | 3/2017 | Pedersen | H04L 63/0442 |
| 2017/0070344 A1 * | 3/2017 | Pedersen | H04L 9/0819 |
| 2017/0070830 A1 * | 3/2017 | Secall | H04W 8/005 |
| 2017/0105076 A1 * | 4/2017 | Gehring | H04R 25/305 |
| 2017/0318400 A1 * | 11/2017 | Westermann | G06F 21/6245 |
| 2017/0374480 A1 * | 12/2017 | Pedersen | G06F 21/73 |
| 2018/0124526 A1 * | 5/2018 | Solum | H04L 63/061 |
| 2018/0167751 A1 * | 6/2018 | Vendelbo | H04R 25/558 |
| 2018/0227678 A1 * | 8/2018 | Pedersen | H04R 25/55 |
| 2019/0191255 A1 * | 6/2019 | Maretti | H04R 25/552 |

* cited by examiner

SECURELY SHARING DATA BETWEEN A HEARING DEVICE, HEARING DEVICE USER, AND DATA STORAGE

CROSS REFERENCE TO RELATED APPLICATION

The present application claims priority to European Patent Application 18176351.7 titled "Securing a Uniform Resource Indicator for Communicating between a Hearing Care Professional and a Hearing Device User," filed on Jun. 6, 2018, which is incorporated herein by reference for its entirety.

TECHNICAL FIELD

The disclosed technology generally relates to securely sharing data between a hearing care professional (HCP) and a hearing device user. In particular, the disclosed technology relates to securely accessing hearing device fitting data stored in data storage before, after, or during a hearing device fitting session.

BACKGROUND

Hearing device users and HCPs want to communicate over the Internet securely. For example, an HCP may want to securely store hearing device fitting data in cloud storage, where it can be accessed by the hearing device user or the HCP. Fitting data is data that relates to settings, parameters, modes, information associated with a hearing device user (e.g., audiogram for a user), or properties associated with a hearing device.

Passwords and usernames are one technique for securing data. For example, patent application WO 2016/078710 discloses a system for granting access rights to data for a hearing aid user by creating a user account on a remote server accessible over the Internet. Passwords or usernames can be circumvented and are not fully secure (e.g., subject to a brute force attack). More generally, passwords are susceptible to frequent and large-scale attacks because passwords can be leaked or illegally.

Other techniques exist to secure data. For example, Pedersen et al. (U.S. Pat. No. 9,608,807) discloses a hearing device system for communicating between a hearing device and a computer. Pedersen's hearing device includes a processing unit that is configured to receive a session request for a session, obtain and store a session key, and encrypt the session key based on a hearing device key. Based on the encrypted session key, the hearing device can communicate with a computing device. However, Pedersen's technology is still subject to attacks and improper access to data. Therefore, there still exists a need to improve security for data and communication.

BRIEF DESCRIPTION OF THE DRAWINGS

The accompanying figures are some implementations of the disclosed technology.

The figures are not drawn to scale and have various viewpoints and perspectives. Some components or operations shown in the figures may be separated into different blocks or combined into a single block for the purposes of discussion. The disclosed technology covers modifications, equivalents, and alternatives falling within the scope of the appended claims.

DETAILED DESCRIPTION

The disclosed technology relates to securely sharing data between an HCP and a hearing device user. For example, a user can use the disclosed technology to securely access data storage storing fitting data for the user's hearing.

The disclosed technology includes a hearing device that has a memory, where the memory stores a key that can be used for encryption and decryption. The key can be a symmetrical key (also referred to as "a symmetrical digital key"). A symmetrical key represents a shared secret between two or more parties (e.g., a prime number or symmetric key algorithm). Anyone who wants to decrypt or encrypt data can use the symmetrical key, e.g., by getting the key from the hearing device. The key is also referred to as a "digital key" because it is digital.

In some implementations, the symmetric key is stored in the hearing device and the hearing device is configured to keep the key secret and encryption or decryption can only occur by requesting the hearing device perform the decrypting or encrypting operation using the key in the memory of the hearing device. Only performing decrypting or encrypting operations on the hearing device can also include envelop encryption, where one key is used to encrypt another key (see FIG. 1B and the corresponding text for more information). Envelop encryption also generates an "encrypted key", where the encrypted key can be stored with encrypted data.

In addition to storing a key, the hearing device can store a uniform resource indicator (URI) in its memory. The URI is a generic string of characters designed for unambiguous identification of a resource. A URI can be a URI to a database, network, web address, computer address, resource, fitting data, or calendar invite stored in the cloud. For example, after conducting a fitting session, the fitting station can generate a URI associated with fitting data from that fitting session, where the URI is associated with the fitting data in data storage. The hearing device user or HCP must use the URI to access the fitting data from the fitting session.

In some implementations, a fitting station, hearing device, or cloud service generates the URI and the URI is associated with a hearing device serial number, a fitting session identification (ID), or user identification number (e.g., medical record number, telephone number, email). The URI can be non-sequential and based on random byte structure, which prevents a malicious user from guessing the URI.

A hearing device user can use the URI and the key to access the fitting data. For example, a user's mobile device paired to the hearing device can use a mobile application to broker communication with data storage (e.g., cloud storage) where fitting data is stored. The hearing device can share the URI, which can proceed to obtain the fitting data from the data storage. In some implementations, the hearing device performs the decryption of the fitting data using its key in memory and only shares the URI with the mobile app. In other implementations, the hearing device provides the symmetrical key to the mobile application for decryption. In yet other implementations, the hearing device can perform envelope encryption to encrypt a received key, where the received key was used to encrypt the fitting data. The encrypted key can be stored with the encrypted data, and the hearing device can be used later to decrypt the encrypted key in order to decrypt the encrypted data.

The disclosed technology can also digitally sign a URI as disclosed in European Patent Application 18176351.7 titled "Securing a Uniform Resource Indicator for Communicating between a Hearing Care Professional and a Hearing Device User," which is incorporated herein by reference in its. In such implementations that included a signed URI, there can be three keys. A first key is a digital key, which is a symmetrical key to encrypt or decrypt fitting data. A second key is a private key used to sign a URI. A third key is a public key used to verify that a URI was signed.

In some implementations, the disclosed technology has at least one technical solution to a data security problem. One technical solution is that by encrypting the fitting data, storing the key and URI in the hearing device, and only allowing access to the encrypted data with the URI and the key, the disclosed technology reduces unwanted or improper access to fitting data. Further, requiring access to both the key and the URI to access fitting data improves security because at least two criteria are required.

Additionally, the disclosed technology reduces (e.g., eliminates) the need for a separate trusted party for encryption and decryption. A trusted part is a party that others trust to generate a keys or security algorithms. Here, the user and the HCP agree to trust the hearing device, and the hearing device because the trusted authority. The HCP, the user, or the hearing device can encrypt/decrypt the fitting data with the key, and these parties agree to trust the key because the chain of title of the key is protected and known (e.g., from the manufacturer to hearing device). Reducing the number of parties involved reduces processing time, increases security, reduces costs, and allows others to use this solution as a "plug-and-play" solution without requiring a separate database or login portal. The chain of title from the hearing device manufacturer to the HCP is secure and makes it difficult for hackers to access.

Figure 1A:
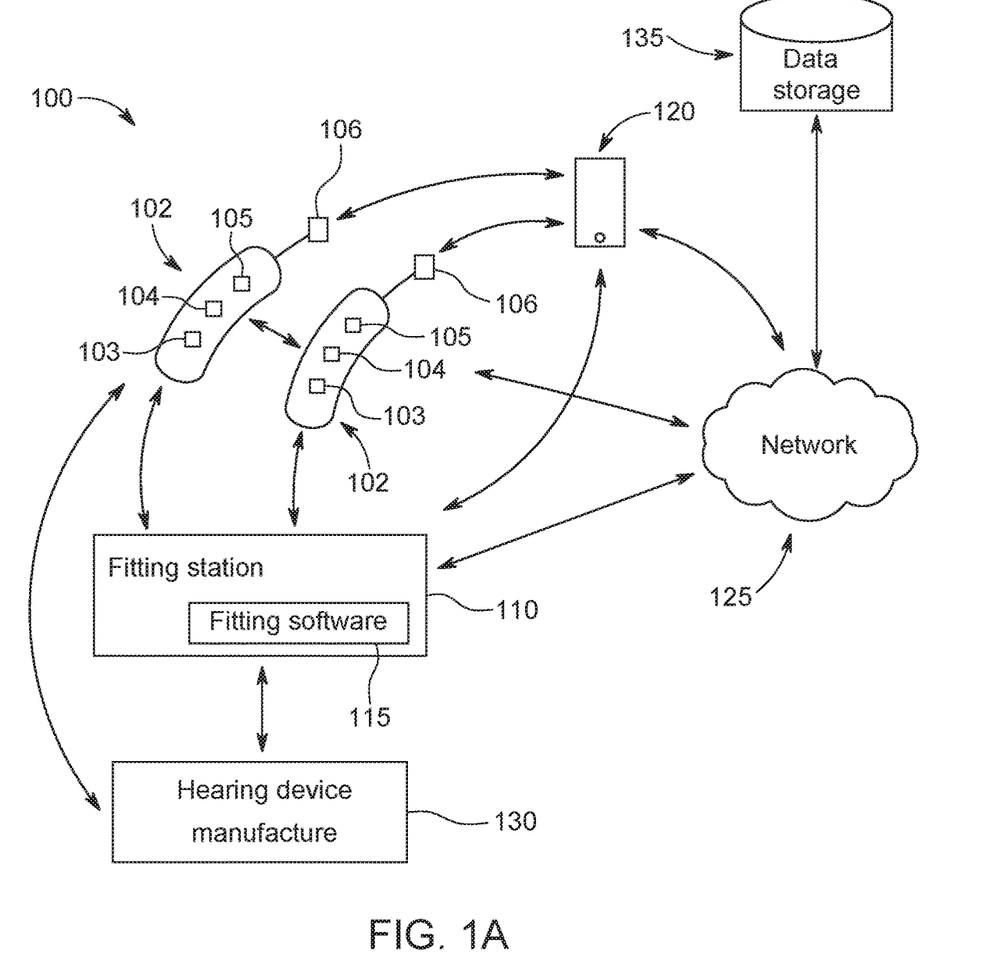
FIG. 1A illustrates a communication environment with hearing devices, a fitting station, an electronic device, a network, and data storage in accordance with some implementations of the disclosed technology.

FIG. 1A illustrates a communication environment 100 with hearing devices 102 (a "hearing device 102" is a single device and "hearing devices 102" is more than one hearing device), a fitting station 110 with fitting software 115, an electronic device 120, a network 125, a hearing device manufacture 130, and data storage 135.

An HCP can use the communication environment 100 to communicate with a hearing device user, where the hearing device user has an electronic device 120 such as a mobile device or personal computer. Because the hearing devices 102 have a limited user interface (e.g., no graphical user interface), the electronic device 120 is used to facilitate interactions between the hearing devices 102 and the user of the hearing devices 102. The communication environment 100 can be used to conduct a fitting session. A fitting session is a session between an HCP and hearing device user where the parties discuss, address, or review hearing issues. For example, the HCP and hearing device user can set up a video conferencing session or Voice-over Internet Protocol (VoIP) session to discuss issues related to hearing devices 102. Although fitting sessions are disclosed in this disclosure, the communication environment 100 can also be used for general electronic communication between the HCP and the hearing device user.

Regarding the hearing devices 102, the hearing devices 102 are devices that provide audio to a user wearing the hearing device. The hearing devices 102 can do this individually or in combination. Some example hearing devices include a hearing aid, headphones, earphones, assisted listening devices, or any combination thereof; and hearing devices include both prescription devices and non-prescription devices configured to be worn on a human head. A hearing aid is a device that provides amplification or attenuation of audio signals to compensate for hearing loss or attenuation functionalities; some example hearing aids include a Behind-the-Ear (BTE), Receiver-in-the-Canal RIC, In-the-Ear (ITE), Completely-in-the-Canal (CIC), or Invisible-in-the-Canal (IIC) hearing aids. A hearing device can also include a cochlear implant, where the cochlear implant has an implant component that is implanted into a person and a device component that communicates with the implant part. The hearing devices 102 can be the same device or different devices (e.g., one hearing device is a hearing aid and the other is a cochlear device).

Each of the hearing devices 102 can include a processor 103, an antenna 104, a memory 105, and a receiver 106. In some implementations, the receiver 106 is a loudspeaker that provides audio output and in other implementations the receiver 106 may not provide an acoustic output because it is part of a cochlear implant that is outputting electronic or magnetic signals. Each of the hearing device 102 components are described below.

The processor 103 processes information for the hearing device 102 and the processor 103 is configured to control the hearing device 102. The processor 103 can include special-purpose hardware such as application specific integration circuits (ASICS), programmable logic devices (PLDs), field-programmable gate arrays (FPGAs), programmable circuitry (e.g., one or more microprocessors microcontrollers), Digital Signal Processor (DSP), appropriately programmed with software and/or computer code, or a combination of special purpose hardware and programmable circuitry. The processor 103 can perform hash functions or hash computations.

In some implementations, the processor 103 can have a processing unit configured to control the hearing device and another processor that is a cryptoprocessor. The cryptoprocessor is a dedicated processor for carrying out cryptographic operations. The cryptoprocessor can be embedded in chip packaging with a physical security that provides a tamper resistance. The physical security measure can be a physical barrier preventing access to the cryptoprocessor or circuitry that prevents access. The cryptoprocessor can also have circuitry or software configured to prevent tampering or unwanted access.

The processor 103 is electronically coupled to memory 105 such as volatile memory or nonvolatile memory. In some implementations, the memory 105 can store a key, a URI, and security algorithms (see FIG. 1B). For example, a hearing device manufacturer 130 can store a digital key in the memory 105. Alternatively, the memory 105 can be configured to store encryption algorithms that the processor 103 can use to generate a key. In some implementations, the memory 105 is physically divided into two separate sections, where one section stores a key or algorithm and another section stores data related to audio modification or digital signal processing.

To wirelessly communicate with other devices, the hearing devices 102 use the antenna 104. The antenna 104 can be a single antenna or an array of antennas. The antenna 104 is configured to transmit and receive wireless communication signals in frequency bands (e.g., in the 2.4 GHz frequency band for Bluetooth Classic™, Bluetooth Low Energy™, or a range of frequencies from 1 to 6 GHz). As shown in FIG. 1, the antenna 104 can be completely inside the housing (e.g., plastic housing). However, the antenna 104 can be partially or completely outside of the housing depending on desired transmission and propagation properties. The hearing device 102 can have more than 1 antenna where each antenna is configured to operate on a different frequency or for a different purpose (e.g., Wi-Fi or Bluetooth™).

In some implementations, the hearing devices 102 are configured to binaurally communicate. For example, the hearing devices 102 can communicate to modify a hearing experience for a user, e.g., implementing beamforming or noise canceling or signal modification. The hearing devices 102 can also be configured to transmit the URI and the digital key to each other, which means the devices can share the URI or digital key. In some implementations, for security reasons, a signal hearing device may store the key and the URI. In other implementations, the hearing devices 102 can exchange or transfer the key or URI from one hearing device to another hearing device.

The hearing devices 102 can include additional components. For example, if the hearing devices 102 are configured for wireless inductive charging, the hearing devices 102 can include a coil to receive a magnetic field. The coil can vary in size, shape and construction depending on the size of the hearing devices 102 and the designed power to be received by the hearing device 102. The hearing devices 102 can have a microphone or microphones. The microphone or microphones can be used for own-voice detection or receiving sound.

With further reference to FIG. 1, the electronic device 120 can be a mobile device, smart phone, tablet computer, laptop computer, desktop computer, a media device, virtual or augmented reality device, vehicle-based computer, wearable computing device, or portable electronic device. The electronic device 120 can include software or an application that controls or communicates with the hearing devices 102. In some implementations, the hearing device 102 or the hearing devices 102 can communicate with the electronic device 120 using an Institute of Electrical and Electronics Engineers (IEEE) 802.11 standard, Bluetooth™, ZigBee™, or a proprietary protocol where signals are propagated between from the antenna 104 to an antenna at the electronic device 120 (e.g., bidirectional, or unidirectional communication). For example, the electronic device 120 can be a smartphone with a mobile application or software program that provides a user interface for the hearing device user.

The fitting station 110 is configured to communicate with the hearing device 102 or the hearing devices 102, e.g., via Bluetooth™ or another wireless communication protocol. The fitting station 110 can be portable (e.g., laptop) or fixed in a location (e.g., a desktop at the HCP's office). The fitting station 110 can be a computer or a terminal connected to a server or cloud computing service. For example, the fitting station 110 can be a computer in a HCP's office (e.g., a home office), where the fitting station 110 is used to fit hearing devices 102. The fitting station 110 is configured to communicate with the hearing device 102 or the hearing devices 102, e.g., via Bluetooth™ or another wireless communication protocol. The fitting station 110 can be portable (e.g., laptop) or fixed in a location (e.g., a desktop at the HCP's office).

The fitting station 110 can include fitting software 115. The fitting software 115 is a set of instructions that can program or adjust the hearing device 102 or the hearing devices 102. The fitting software 115 can incorporate user experience values or user experience settings such as how a user feels or how a user perceived a sound (e.g., dog bark, conversation, high pitched noise) or a sound environment (e.g., movie theater, quite room). The fitting software 115 can personalize settings to accommodate individual user preferences and listening needs. The fitting software 115 can adjust hearing device settings for speech, own voice, overall loudness, and individual phonemes for speech recognition and intelligibility. The fitting software 115 can also generate visual displays or graphical user interfaces for the hearing device user and the HCP. The visual displays can include information about the hearing device 102 or the hearing devices 102.

The fitting software 115 is configured to generate a URI, where the URI can be read or used by a computer. Although the fitting software 115 can generate the URI, the fitting station 110 can have other software that is configured to generate a URI.

The network 125 enables the hearing devices 102 to send and receive information from the Internet via the electronic device 120. For example, the network 125 can be a Wi-Fi™ network or a networking implementing an Institute of Electrical and Electronics Engineers (IEEE) 802.11 standard and the electronic device 120 can connect with network 125 to receive and send information, and the electronic device 120 can also send and receive information to and from the hearing devices 102 (or both hearing devices 102). In another example, the hearing devices 102 can communicate directly with the network 125, e.g., if network 125 is a Bluetooth™ network or 802.11 IEEE standard wireless communication network, where the hearing devices 102 are configured to communicate with the network 125.

Also, the network 125 can be a single network, multiple networks, or multiple heterogeneous networks, such as one or more border networks, voice networks, broadband networks, service provider networks, Internet Service Provider (ISP) networks, and/or Public Switched Telephone Networks (PSTNs), interconnected via gateways operable to facilitate communications between and among the various networks. The network 125 can include communication networks such as a Global System for Mobile (GSM) mobile communications network, a code/time division multiple access (CDMA/TDMA) mobile communications network, a $3^{rd}$, $4^{th}$ or $5^{th}$ generation (3G/4G/5G) mobile communications network (e.g., General Packet Radio Service (GPRS/EGPRS)), Enhanced Data rates for GSM Evolution (EDGE), Universal Mobile Telecommunications System (UMTS), or Long Term Evolution (LTE) network), or other communications network such as a Wireless Local Area Network (WLAN).

The data storage 135 is data storage accessible directly or via the Internet. In some implementations, the data storage 135 includes data that is stored in logical pools, where the physical storage spans multiple servers (e.g., different locations) and the physical storage is owned by a company (e.g., cloud storage). The data storage 135 can be accessed through a computer or cloud computer service with a web service application programming interface (API) or by applications that utilize the API such as a cloud desktop storage. An HCP can access the data storage 135 using, e.g., a fitting station 110 or another computer. The data storage 135 can be accessible by all HCPs such that they can easily share or access fitting data for users. The data storage 135 can also be remote data storage because it can be located away from the HCP or the user. Remote generally means the located or stored away from a computer, e.g., located on the cloud or in data storage accessible over the Internet. For example, the data storage 135 can be in another area of a room, in another city, or another country relative to the hearing devices 102.

Figure 1B:
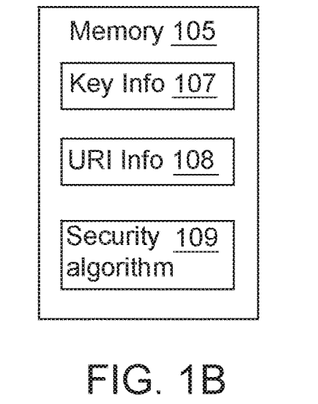
FIG. 1B illustrates a more detailed schematic view of the memory inside of the hearing devices from FIG. 1A in accordance with some implementations of the disclosed technology.

FIG. 1B illustrates a more detailed schematic view of the memory 105 inside of the hearing device 102 from FIG. 1A. The memory 105 can include key information (key info.) 107, URI information (URI info.) 108, and security algorithm 109 information. In some implementations, the security algorithm 109 is information only access by a cryptoprocessor such that the security algorithm 109 information and the cryptoprocessor form a hardware encryption chip, where the hardware encryption chip is physically protected and only accessible and useable on the hearing device (also referred to as a "hardware-based" encryption chip).

The key information 107 can include a digital key such as a symmetric key. The processor 103 can read or access this key by accessing the memory 105. In some implementations, the memory 105 is configured to prevent the key information 107 from leaving the hearing device 102 such that all requests to use or the key will only be executed at the hearing device 102. The memory 105 can also store security algorithms 109 that are used to generate a hearing device's own key, where multiple keys can be generated and each key can be difference. The key information 107 can also include a private key, public key, or combination of private and public keys as described in European Patent Application 18176351.7. In some implementations, the hearing device manufacturer 130 installs a key used for encryption and decryption. In some implementations, as described in European Patent Application 18176351.7, the hearing device manufacturer installs a private key and public key in the memory 105 when the hearing device is manufactured.

The URI information 108 can include a URI. The URI can be a "Globally Unique Identifier" (GUID), Universally Unique Identifier (UUID), or a Uniform Resource Locator (URL). For example, the URI can be a URL associated with a fitting data in the data storage 135. In some implementations, the URI can be 128-bit integer number used to identify resources (e.g., file location, server address, fitting data in cloud storage, or location on a computer network or in a computing device). The URI can include or be associated with hearing device identification such as serial number, product number, or other number associated with the hearing device or the hearing devices, a fitting session identification such as a number associated with a fitting session for the hearing devices or devices, or information deemed necessary by the HCP. In some implementations, the fitting software 115 generates the URI (e.g., a computer for the HCP with fitting software for fitting a hearing device). The fitting station can transmit the URI to the hearing device 102.

The security algorithm 109 information can include classes, libraries, and other instructions for carrying out computer operations related to security. The security algorithm 109 can include a cryptographic hash function. The security algorithm 109 can include a cryptographic hash function such as Triple Data Encryption Algorithm (TDEA) or Advanced Encryption Standard (AES) algorithm. In some implementations, the security algorithm 109 information and the cryptoprocessor can form a hardware encryption chip, where the hardware encryption chip is physically protected (e.g., with shielding) and only accessible and useable on the hearing device.

The security algorithm 109 can also include information for performing envelop encryption. Envelop encryption includes receiving a key and using the digital key stored on the hearing device to generate an encrypted key. For example, a fitting station or fitting software can encrypt fitting data using a first key. The fitting station can send the first key to the hearing device, and the hearing device can use its digital key to generate an encrypted digital key, where the encrypted digital key is the first key encrypted by the digital key (also referred to as a "encrypted key"). The hearing device 102 can transmit the encrypted digital key from the hearing device to another device or storage. Because the encrypted digital key is derived from the digital key stored on the hearing device, it is required to have access to the digital key on the hearing device or have the hearing device to decrypt the encrypted digital key. Envelope encryption has a technical benefit in that the hearing device does not need to perform the encrypting and decrypting operations for the fitting data. Rather, the hearing device encrypts only the received key that performed the encryption operations and another device performs the encryption or decryption of fitting data (e.g., a mobile device or computer with more processing power and memory than a hearing device). With envelope encryption the hearing device can use less bandwidth to send information between the hearing device and another device because only information related to the encryption and decryption of the key is necessary.

In some implementations, the digitally signing algorithms are incorporated into the security algorithm 109. See European Patent Application 18176351.7 titled "Securing a Uniform Resource Indicator for Communicating between a Hearing Care Professional and a Hearing Device User." For example, the hearing device can also digitally sign a link using a stored private key. In some implementations, the private key used to the sign the URI can be different than the digital key used to encrypt or decrypt the data.

Figure 2:
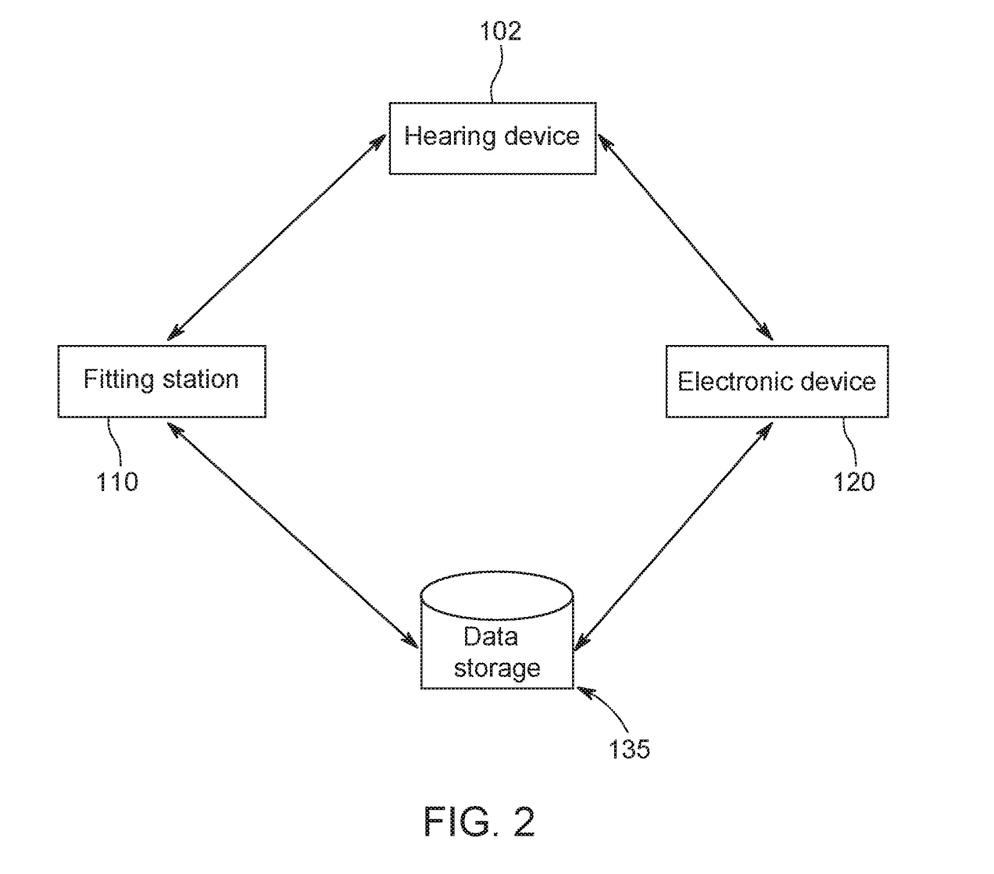
FIG. 2 illustrates a schematic block diagram for sharing data between a fitting station, hearing device, electronic device, and data storage in accordance with some implementations of the disclosed technology.

FIG. 2 illustrates a schematic block diagram for sharing data between the fitting station 110, the hearing device 102, the electronic device 120, and the data storage 135. The fitting station 110, the electronic device 120, the hearing device 102, and the data storage 135 can communicate, for example, to exchange a URI, fitting data, perform encryption or decryption operations, or to share a key. The double-headed arrows in FIG. 2 illustrate that these components can communicate wirelessly, through a network (e.g., the network 125), or through a wired network.

In some implementations, the fitting station 110 receives or generates fitting data and encrypts the data at the fitting station. The fitting station encrypts the data using a key (e.g., symmetrical key) and creates a URI (e.g., a link) that is associated with the location (e.g., in data storage) for the fitting data. The fitting station 110 can send the key and the URI to the hearing device for storage. The hearing device can store the URI and the key. Alternatively, the hearing device can store the key and only perform encryption of decryption operations on the hearing device such that the key never leaves the hearing device.

When an HCP receives a hearing device at his or her office and conducts a fitting session with a user of the hearing device, the HCP can also encrypt the fitting data and generate a URI. The fitting station 110 can also store the encrypted fitting data on the data storage. For example, the HCP can have an agreement with a cloud service provider regarding storage of fitting data or other customer information.

Figure 3:
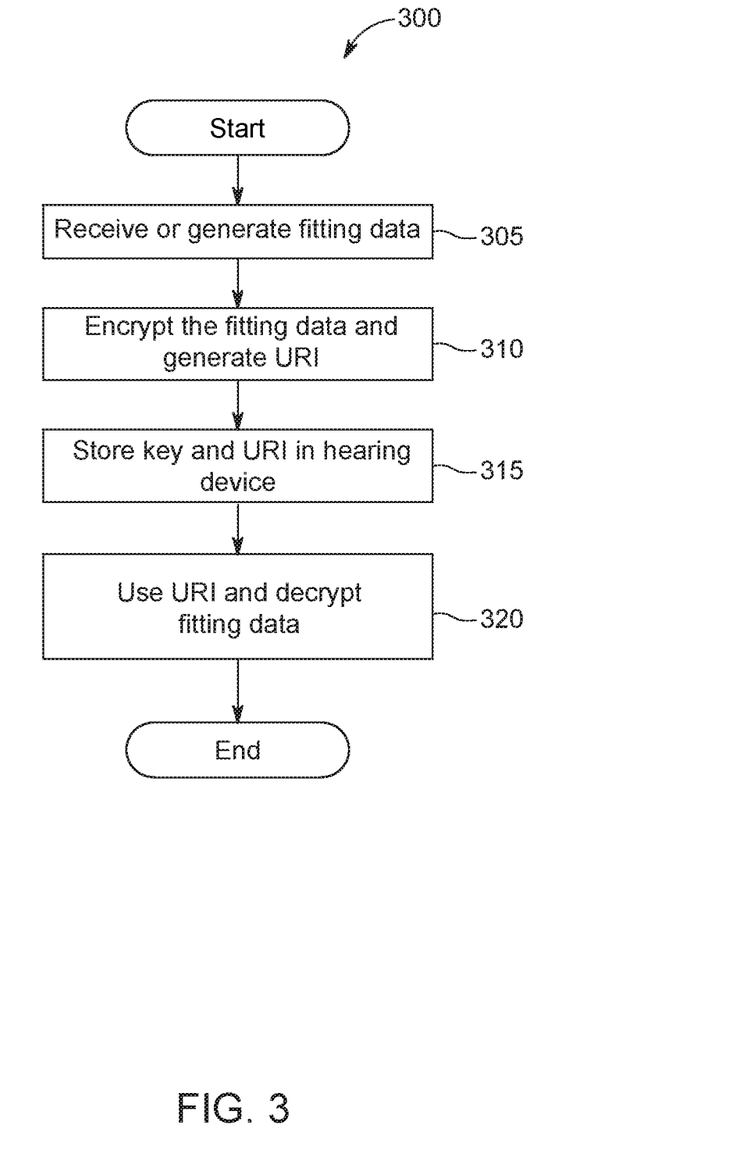
FIG. 3 is a block flow diagram illustrating a process for sharing data between an HCP, a hearing device user, and data storage in accordance with some implementations of the disclosed technology.

FIG. 3 is a block flow diagram illustrating a process 300 for sharing data between an HCP, a hearing device user, and data storage. The process 300 can incorporate the implementations described in FIGS. 1A-1B and FIG. 2, e.g., the fitting station 110, the fitting software 115, the hearing device 102 or the hearing devices 102, the electronic device 120, the network 125, the hearing device manufacturer 130, and the data storage 135. The process 300 can start automatically once an HCP begins a fitting session with a hearing device user. In some implementations, the HCP or hearing device user can manually start the process 300 when a user turns on his or hearing devices or activates a mobile application, where the mobile application is running on a user's device.

At receive or generate operation 305, the fitting station 110 receives or generates fitting data. For example, the HCP can begin by downloading fitting data from the Internet or cloud storage. The HCP can also determine diagnostic or current settings for a hearing device that a user is wearing or should wear based on communication with the hearing device or user. The HCP can electronically receive the data or input the data into the fitting station. In some implementations, the HCP generates or receives an audiogram for a hearing device user. The HCP can also generate the fitting data by conducting a fitting session. The HCP can also conduct a distance fitting session where the HCP is one location and the user located away from the HCP, where the HCP and user communicate via network. The fitting station 110 can receive data from the hearing device itself, and the fitting data can indicate current settings or preferred settings for the hearing device (e.g., volume settings, connectivity settings), where preferred settings where set by the user.

In some implementations of the receive or generate operation 305, the fitting station 110 also receives fitting data from a user's mobile device. For example, a user may use his or her mobile device with the hearing device, and the mobile device can record information related to hearing device performance, settings, or environment (e.g., surrounding sounds, previous geolocation of the hearing devices, maximum or minimum values detected). The fitting station 110 can also receive bibliographic information or medical information that is also considered fitting data (e.g., age, weight, length of hearing loss, other data related to medical conditions for the user). Also, the fitting station 110 can receive information from a cloud service that is storing fitting data for a user. For example, a user may store his or her information in cloud storage and the fitting station 110 can receive this information from cloud storage in the receive or generate operation 305.

At encrypt and generate URI operation 310, the hearing device or the fitting station encrypts the fitting data and generates a URI associated with the encrypted data. To encrypt the fitting data, the hearing device or the fitting station can use a digital key and security algorithms. If the key is stored in the hearing device memory, the hearing device can use it to encrypt the data locally on the hearing device. A hearing device can store the digital key based on installation from a hearing device manufacture or the hearing device can generate the digital key based on key generation algorithms stored in memory. Alternatively, the fitting station can receive the digital key from the hearing device, and the fitting station can encrypt the fitting data with the received key.

In some implementations, the encrypt and generate URI operation 310 includes envelope encryption. Envelope encryption can include the fitting station using a first key to encrypt fitting data. The fitting station can then transmit this first key to the hearing device, and the hearing device can encrypt the first key with its digital key to generate a first encrypted key from the first key. The hearing device can send the encrypted first key to storage to be stored with the fitting data, back to the fitting station, or to another device. As discussed in other operations, the encrypted digital key can be used to decrypt the fitting data.

At encrypt and generate URI operation 310, the fitting station or the hearing device also generates a URI for the encrypted fitting data. For example, the fitting software 115 can generate the URI. The URI can be a URL, GUID, or a UUID. For example, the URI can be a location of the fitting data in data storage (e.g., cloud storage). The URI can be associated with the hearing device (e.g., serial number for the hearing device); the user of the hearing device (e.g., name, medical record number, patient ID); or a fitting session number (e.g., a number that identifies the date, time, or location of the fitting session). The URI can also be randomized or comprises on anonymized digits or information.

The fitting station 110 or the hearing device can generate a new URI for each new fitting session. For example, the fitting station 110 or the hearing device can generate a first URI associated with a first session and then generate a second URI associated with a second fitting session, where the second fitting session occurred after the first fitting session. Also, the fitting station 110 or hearing device can generate a URI that expires. For example, the fitting station 110 or the hearing device can generate a URI that expires in 1 week, 1 month, or 1 year. To include an expiration, the fitting station or the hearing device can generate the URI as described in European Patent Application 18176351.7 titled "Securing a Uniform Resource Indicator for Communicating between a Hearing Care Professional and a Hearing Device User." For example, the digitally signed URI can include a timestamp or expiration based on the digital signing process.

At the store key and URI operation 315, the fitting station 110 can transmit the URI to the hearing device 102. The fitting station 110 can transmit the URI using Wi-Fi™ or Bluetooth™ or another wireless communication protocol. In some implementations, the transmit URI operation 315 occurs in an HCP's office and when the HCP has received a pair of hearing devices that the HCP intends to give to a user. Because the HCP received the hearing device at his or her office from a hearing manufacture and the HCP is considered a trusted authority (as well as the hearing device manufacture), the operation includes built in security measures to prevent others from generating false URIs. Regarding the key, the hearing device may already store the key. For example, the hearing device manufacturer may have installed it on the hearing device. Alternatively, the hearing device can generate a new key using a key generator.

At use URI and decrypt fitting data in storage operation 320, the hearing device or an electronic device use the URI and decrypt the fitting data. In some implementations, an electronic device paired to the hearing device requests the URI from the hearing device and receives it. The electronic device can be a mobile device and the electronic device can use an application to request the URI. The electronic device can also be a user's personal computer configured to communicate with the hearing device. The electronic device can also determine if the URI was digitally signed during the use URI and decrypt fitting data in storage operation 320. The electronic device can use the URI to access the encrypted data and begin the decryption process.

To decrypt data, the hearing device or the electronic device can use the symmetrical key. For example, the hearing device perform the decrypting or encrypting operation using the key in the memory of the hearing device. In some implementations, the key only resides in the hearing device and decryption operations only happen on the hearing device. Once the fitting data is decrypted, it can be referred to as decrypted fitting data. In other implementations, an electronic device can access the key or receive the key from the hearing device to perform decryption. Additionally, the hearing device can perform envelope encryption to decrypt an encrypted to key. The decrypted key can be used to decrypt the fitting data.

In some implementations, the decrypted fitting data includes information used to modify the hearing device. The decrypted fitting data can include settings for the hearing device, modes for the hearing device, or parameters that modify the hearing device. The mobile device can transmit these parameters to the hearing device, and the hearing device can modify itself according to these parameters. In some implementations, the encrypted fitting data includes settings suggested by an HCP. In other implementations, the encrypted fitting data can include tasks or requests to the hearing device user. For example, the fitting data can include a request to collect certain information from the hearing device or ask the user to perform certain operations or record observations in response to a test of the hearing device.

After the operation 320, the process 300 can stop or be repeated partially or completely. In some implementations, the process 300 occurs continuously while the HCP is sending URIs or information to an electronic device or a user associated with a customer profile.

Figure 4A:
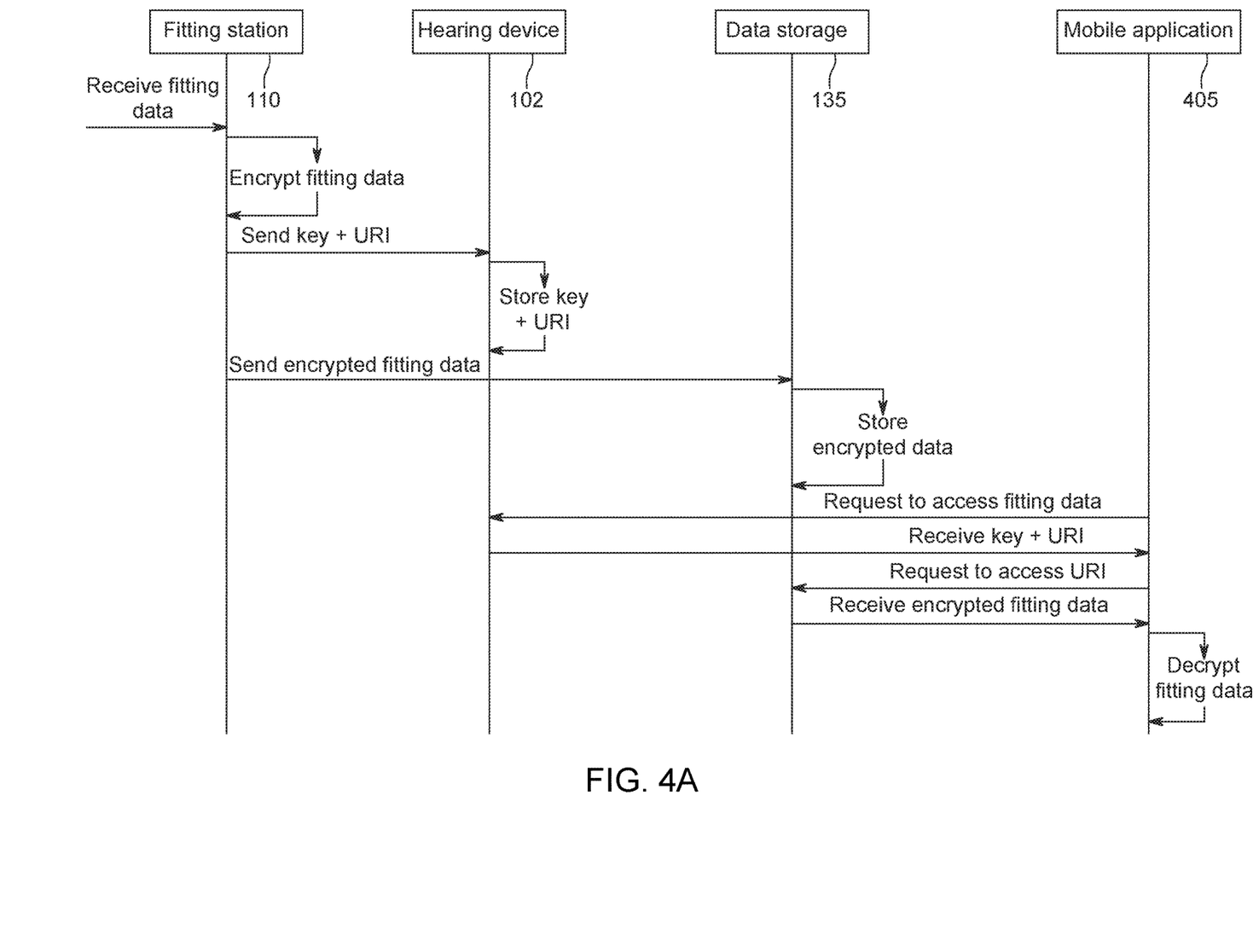
FIGS. 4A and 4B illustrate operations for sharing fitting data between a fitting station and a mobile application in accordance with some implementations of the disclosed technology.
Figure 4B:
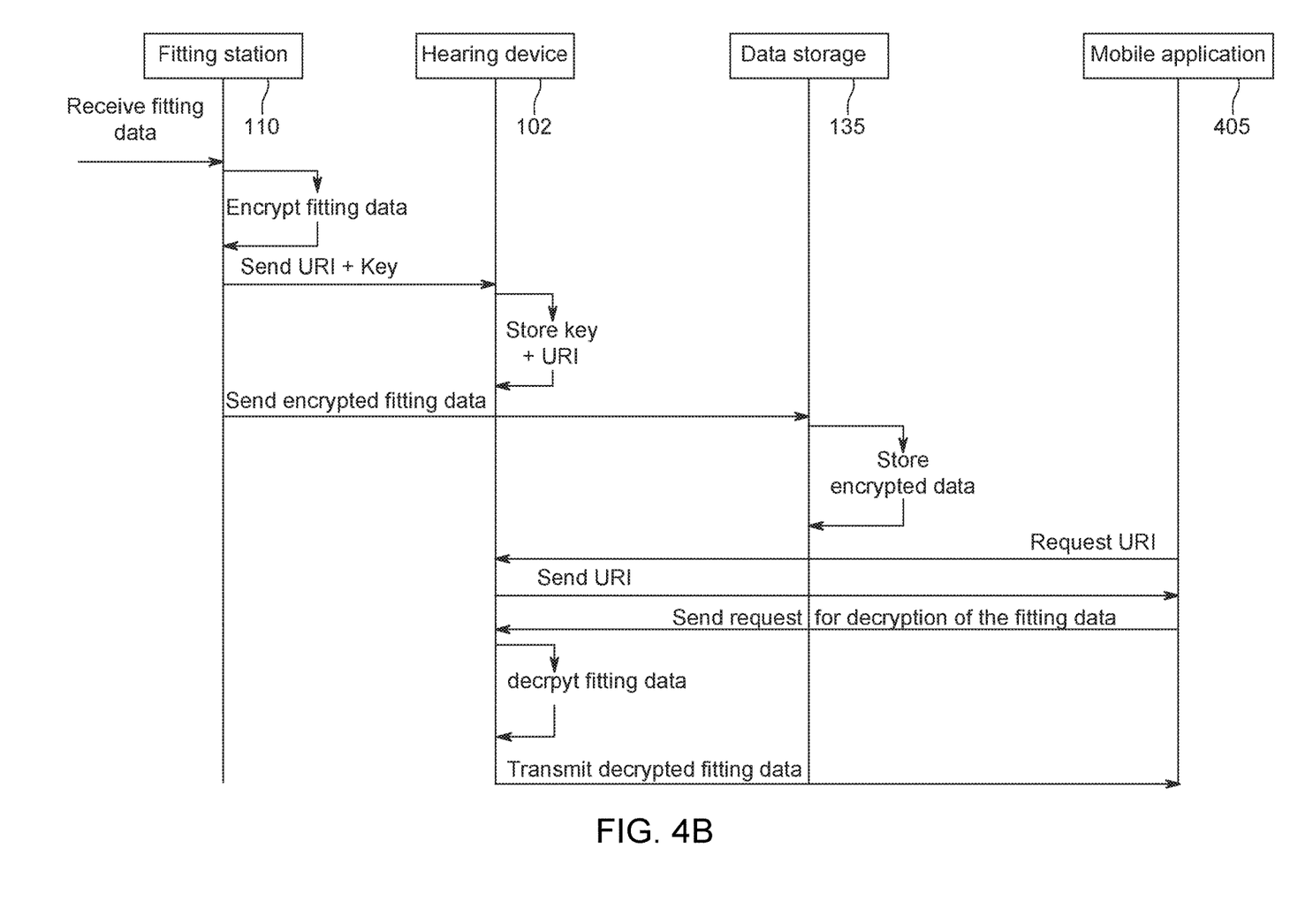

FIGS. 4A and 4B illustrate operations for sharing fitting data between a fitting station and a mobile application. The examples include the fitting station 110, the hearing device 102, the data storage 135, and a mobile application 405. FIG. 4B describes the same process as FIG. 4A, except the decryption is limited to be performed on the hearing device.

As show in FIG. 4A, the fitting station receives or generates fitting data. The fitting station encrypts the fitting data at the fitting station using a key or access to the key on the hearing device. The fitting station can associate a URI with the encrypted fitting data. For example, the fitting station can generate a URL that refers to the location of the encrypted fitting data in cloud storage. Although the fitting station performs the encrypting operations, the hearing device can also perform these operations, where the fitting station would send the unencrypted fitting data to the hearing device for encryption.

Further shown in FIG. 4A, the fitting station can send the encrypted data to data storage where it can be access by an HCP, user, or other party that has the URI. The data storage can store the encrypted fitting data (e.g., a cloud storage service). Then, using a mobile application on a mobile device, a user can request to access or read fitting data from the hearing device. In response to this request, the hearing device can allow the mobile application to receive the key and the URI. In some implementations, the mobile application receives access to the key and not the actual key, e.g., decryption is performed on the hearing device. Using the URI, the mobile application can request the encrypted fitting data and decrypt it. The mobile application can decrypt fitting data locally (e.g., on the mobile device) and provide it to the user or the mobile application can use the fitting data to adjust the hearing device.

In FIG. 4B, the decryption is only performed on the hearing device. Also, although not shown in FIG. 4B, the encryption and decryption operations can refer to envelope encryption where a key is encrypted and decrypted as part of the secure communication process. For example, a first key on the fitting station is used to encrypt the fitting data when it is received or generated. The fitting station then sends the first key to the hearing device. The hearing device encrypts the first key by using its key, which generates an "encrypted key". The encrypted key is stored with the fitting data, e.g., the fitting station sends it to data storage with the encrypted fitting data. To decrypt the fitting data, it is required to have access to the hearing device key to decrypt the encrypted key.

CONCLUSION

Unless the context clearly requires otherwise, throughout the description and the claims, the words "comprise," "comprising," and the like are to be construed in an inclusive sense, as opposed to an exclusive or exhaustive sense; in the sense of "including, but not limited to." As used herein, the terms "connected," "coupled," or any variant thereof means any connection or coupling, either direct or indirect, between two or more elements; the coupling or connection between the elements can be physical, logical, electronic, magnetic, electromagnetic, or a combination thereof. Additionally, the words "above," and "below," and words of similar import, when used in this application, refer to this application and not to any portions of this application. Where the context permits, words in the above Detailed Description using the singular or plural number may also include the plural or singular number respectively. The word "or," in reference to a list of two or more items, covers all the following interpretations of the word: any of the items in the list, all the items in the list, any combination of the items in the list, or a single item from the list.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements. Although fitting sessions are disclosed in this disclosure, the communication environment 100 can also be used for general electronic communication between an HCP and a hearing device user.

As another example, the electronic device 120 communicate with hearing device to perform encryption or decryption. For example, a user can communicate some information to the electronic device 120 or the electronic device 120 can generate some information. The electronic device 120 can transmit this information to the hearing device 102, and the hearing device 102 encrypt it. The electronic device 120 can also generate a URI, for example, the electronic device can generate a URI that relates to cloud storage for user information. The electronic device 120 can transmit this URI to the hearing device 102. If the fitting station 110 wants to access the encrypted information, it would need the key stored on the hearing device (e.g., with possession of the hearing device or a prior key transfer from the hearing device) and the URI from the hearing device.

The terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim.

The techniques, algorithms, and operations introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, optical disks, compact disc read-only memories (CD-ROMs), magneto-optical disks, read-only memories (ROMs), random access memories (RAMs), erasable programmable read-only memories (EPROMs), electrically erasable programmable read-only memories (EEPROMs), magnetic or optical cards, flash memory, or other type of media such as machine-readable medium suitable for storing electronic instructions. The machine-readable medium includes non-transitory medium, where non-transitory excludes propagation signals. For example, a processor can be connected to a non-transitory computer-readable medium that stores instructions for executing instructions by the processor such as instructions to generate, digitally sign, verify, or use a URI. The instructions can also include operations for encrypting or decrypting fitting data using a symmetric key.

| Reference list | |
|---|---|
| Communication environment | 100 |
| Hearing device or hearing devices | 102 |
| Processor | 103 |
| Antenna | 104 |
| Memory | 105 |
| Receiver | 106 |
| Key Information | 107 |
| URI information | 108 |
| Security Algorithm | 109 |
| Fitting Station | 110 |
| Fitting Software | 115 |
| Electronic Device | 120 |
| Network | 125 |
| Hearing Device Manufacture | 130 |
| Data Storage | 135 |
| Generated Uniform Resource Indicator (URI) | 202 |
| Process | 300 |

We claim:

1. A method to communicate with a hearing device, the method comprising:
   receiving or generating fitting data at a fitting station,
      wherein the fitting data includes fitting session information for a hearing device or a user and at least one of user information for the user of the hearing device and parameters or settings for the hearing device;
   encrypting the fitting data with a first digital key, the encrypted fitting data stored in a remote data storage;
   generating, at the fitting station, a uniform resource indicator (URI) that identifies the encrypted fitting data stored in the remote data storage,
      wherein the URI provides access to the encrypted fitting data stored in the remote data storage;
   digitally signing, with a cryptoprocessor on the hearing device, the URI with a second digital key; and
   storing, on the hearing device, the digitally signed URI,
   wherein the hearing device is configured to:
      binaurally communicate with an additional hearing device; and
      transmit the URI and the second digital key to the additional hearing device.

2. The method of claim 1, the method further comprises:
   receiving, at an electronic device communicatively coupled to the hearing device, the digitally signed URI from the hearing device.

3. The method of claim 1, the method further comprising:
   receiving the digitally signed URI and the second digital key at an electronic device communicatively coupled to the hearing device;
   receiving, at the electronic device, the encrypted fitting data based on the digitally signed URI;
   decrypting, at the electronic device, the encrypted fitting data based on the second digital key; and
   transmitting instructions from the electronic device to the hearing device to modify the hearing device,
      wherein the instructions are based on the decrypted fitting data.

4. The method of claim 3, wherein the electronic device is a mobile phone configured to use a mobile application, and wherein the mobile application is configured to communicate between the hearing device and the electronic device.

5. The method of claim 1, wherein the hearing device is configured to perform envelope encryption.

6. The method of claim 1, wherein the first digital key is a symmetric key, wherein a hearing device manufacturer stored the symmetric key on the hearing device during production of the hearing device, or wherein the first digital key is a public key.

7. The method of claim 1, wherein the first digital key is stored on the hearing device.

8. The method of claim 1, wherein URI is associated with a fitting session, a hearing device serial number, or the user information.

9. The method of claim 1, wherein the hearing device is a hearing aid.

10. A non-transitory computer-readable medium storing instructions that, when executed by a processor, cause a device to perform operations, the operations comprising:
   receiving or generating fitting data at a fitting station,
      wherein the fitting data includes fitting session information for a hearing device or a user and at least one of user information for the user of the hearing device and parameters or settings for the hearing device;
   encrypting, at the fitting station, the fitting data with a first digital key, the encrypted fitting data stored in a remote data storage;
   generating, at the fitting station, a uniform resource indicator (URI) that identifies the encrypted fitting data stored in the remote data storage, wherein the URI provides access to the encrypted fitting data stored in the remote data storage, wherein the remote data storage is remote from the fitting station and the hearing device;

transmitting the URI to the hearing device for storage, wherein the remote data storage is configured to enable access to the encrypted data only based on the URI;

receiving the URI on the hearing device;

signing digitally, with a second digital key, the URI with a cryptoprocessor of the hearing device; and storing the digitally signed URI in the hearing device, wherein the hearing device is configured to:
   binaurally communicate with an additional hearing device; and
   transmit the URI and the second digital key to the additional hearing device.

11. The non-transitory computer-readable medium of claim 10, wherein the operations further comprise:

receiving, at an electronic device, the signed URI from the hearing device;

transmitting from the electronic device a request to the remote data storage to access the encrypted data, wherein the request is based on the signed URI;

receiving, at the electronic device, the encrypted data;

transmitting the encrypted fitting data from the electronic device to the hearing device and requesting that the hearing device decrypt the encrypted fitting data at the hearing device;

decrypting, at the hearing device, the encrypted fitting data based on the second digital key stored in the hearing device; and transmitting the decrypted data to the electronic device.

12. The non-transitory computer-readable medium of claim 10, wherein the second digital key was stored in a memory for the hearing device by a manufacturer of the hearing device at a time of manufacture for the hearing device, and wherein the cryptoprocessor is configured to use the second digital key.

13. A hearing device comprising:
a microphone;
a receiver configured to provide sound information;
an antenna configured to wirelessly communicate with an electronic device; and
a processor configured to communicate with a memory, wherein the memory is configured to store a key, and wherein the memory stores instructions that, executed by the processor, cause the hearing device to perform operations, the operations comprising:
   providing access to a uniform resource indicator (URI) associated with encrypted fitting data, wherein the encrypted fitting data is associated with parameters or settings for a hearing device, user information for a user of the hearing device, or a fitting session information for the hearing device; and
   providing access to the stored key; and
a cryptoprocessor that is separate from the processor, that is dedicated for carrying out cryptographic operations, and that is configured to digitally sign the URI based on the key,
wherein the hearing device is configured to:
   binaurally communicate with an additional hearing device; and
   transmit the URI and the key to the additional hearing device.

14. The hearing device of claim 13, wherein the key was stored in a memory for the hearing device by a manufacturer of the hearing device at a time of manufacture for the hearing device.

15. The hearing device of claim 13, wherein the electronic device is a mobile phone configured to use a mobile application, and wherein the mobile application is configured to communicate between the hearing device and the electronic device.

16. The hearing device of claim 13, wherein the cryptoprocessor is physically protected and only accessible and useable on the hearing device.

* * * * *